(12) United States Patent
Hoffman

(10) Patent No.: US 7,120,222 B2
(45) Date of Patent: Oct. 10, 2006

(54) CT IMAGING SYSTEM WITH MULTIPLE PEAK X-RAY SOURCE

(75) Inventor: David M. Hoffman, West Berlin, WI (US)

(73) Assignee: General Electric Company, Schnectady, NY (US)

( * ) Notice: Subject to any disclaimer, the term of this patent is extended or adjusted under 35 U.S.C. 154(b) by 103 days.

(21) Appl. No.: 10/250,132

(22) Filed: Jun. 5, 2003

(65) Prior Publication Data

US 2004/0247082 A1 Dec. 9, 2004

(51) Int. Cl.
- H05G 1/02 (2006.01)
- H01J 35/06 (2006.01)
- G21K 3/00 (2006.01)

(52) U.S. Cl. .......................... 378/5; 378/16; 378/98.9; 378/124; 378/134; 378/157; 378/158

(58) Field of Classification Search .................... 378/5, 378/16, 19, 92, 98.9, 98.11, 124, 134, 137, 378/138, 144, 156–159, 115, 116, 143, 57
See application file for complete search history.

(56) References Cited

U.S. PATENT DOCUMENTS

| | | | | |
|---|---|---|---|---|
| 2,350,642 A * | 6/1944 | Schwarzer | ................. | 378/124 |
| 2,597,498 A * | 5/1952 | Kerkhoff | ................. | 378/124 |
| 3,610,984 A * | 10/1971 | Seki et al. | ................. | 378/125 |
| 4,065,689 A * | 12/1977 | Pleil | ................. | 378/134 |
| 4,445,226 A * | 4/1984 | Brody | ................. | 378/98.9 |
| 4,686,695 A * | 8/1987 | Macovski | ................. | 378/146 |
| 4,823,371 A * | 4/1989 | Grady | ................. | 378/134 |
| 4,963,746 A * | 10/1990 | Morgan et al. | ................. | 250/363.02 |
| 5,204,888 A * | 4/1993 | Tamegai et al. | ................. | 378/53 |
| 5,335,255 A * | 8/1994 | Seppi et al. | ................. | 378/4 |
| 5,485,492 A * | 1/1996 | Pelc | ................. | 378/5 |
| 5,490,196 A * | 2/1996 | Rudich et al. | ................. | 378/101 |
| 5,511,105 A * | 4/1996 | Knott | ................. | 378/134 |
| 5,570,403 A * | 10/1996 | Yamazaki et al. | ................. | 378/5 |
| 5,661,774 A * | 8/1997 | Gordon et al. | ................. | 378/101 |
| 6,008,493 A | 12/1999 | Shao et al. | ................. | 250/363.04 |
| 6,036,362 A * | 3/2000 | Schmitt | ................. | 378/206 |
| 6,104,781 A * | 8/2000 | Buchmann | ................. | 378/101 |
| 6,188,747 B1 * | 2/2001 | Geus et al. | ................. | 378/124 |
| 6,226,352 B1 * | 5/2001 | Salb | ................. | 378/98.9 |
| 6,229,870 B1 * | 5/2001 | Morgan | ................. | 378/9 |
| 6,246,747 B1 * | 6/2001 | Wear et al. | ................. | 378/98.9 |
| 6,285,740 B1 | 9/2001 | Seely et al. | ................. | 378/98.9 |
| 6,410,920 B1 | 6/2002 | Shao et al. | ................. | 250/363.04 |

(Continued)

OTHER PUBLICATIONS

B. D. Cullity. Elements of X-Ray Diffraction, second edition (Reading, MA: Addison-Wesley, 1978), p. 6-21.*

(Continued)

Primary Examiner—Allen C. Ho
(74) Attorney, Agent, or Firm—Peter J. Vogel

(57) ABSTRACT

An x-ray source (32) for performing energy discrimination within an imaging system (10) includes a cathode-emitting device (82) emitting electrons and an anode (81) that has a target (80) whereupon the electrons impinge to generate an x-ray beam (93) with multiple x-ray quantity energy peaks (116 and 120). A method of performing energy discrimination in the imaging system (10) includes emitting the electrons. The x-ray beam (93) with the x-ray quantity energy peaks (116 and 120) is generated. The x-ray beam (93) is directed through an object (44) and is received. An x-ray image having multiple energy differentiable characteristics is generated in response to the x-ray beam (93).

15 Claims, 4 Drawing Sheets

U.S. PATENT DOCUMENTS

| | | | |
|---|---|---|---|
| 6,480,572 B1* | 11/2002 | Harris et al. | 378/136 |
| 6,597,758 B1* | 7/2003 | Rosner | 378/53 |
| 6,614,878 B1* | 9/2003 | Bogatu et al. | 378/158 |
| 6,735,273 B1* | 5/2004 | Flohr et al. | 378/5 |
| 2003/0195416 A1* | 10/2003 | Toth | 600/427 |

OTHER PUBLICATIONS

B. D. Cullity. Elements of X-Ray Diffraction, second edition (Reading, MA: Addison-Wesley, 1978), p. 509-511.*

* cited by examiner

CT IMAGING SYSTEM WITH MULTIPLE PEAK X-RAY SOURCE

CROSS REFERENCE TO RELATED APPLICATIONS

The present invention is related to U.S. patent application Ser. No. 10/064,775, filed on Aug. 15, 2002, now U.S. Pat. No. 6,819,738, and entitled "A Hybrid Scintillator/Photo Sensor and Direct Conversion Detector", which is incorporated by reference herein.

BACKGROUND OF INVENTION

The present invention relates generally to multi-slice computed tomography (CT) imaging systems, and more particularly, to a system and method of performing energy discrimination therein.

In computed topography (CT) imaging portions of a patient are scanned and density of materials contained therein are determined for various diagnostic and evaluation purposes. There is a continuous effort to increase CT imaging system scanning capabilities. Specifically, in CT imaging it is desirable not only to be capable of determining density of scanned materials, but also to be able to distinguish between materials or combinations of materials that have similar densities.

For example, in certain testing procedures, in order to enhance visibility of blood and to better differentiate blood from other tissues or undesirable deposits within a vessel or organ, Iodide may be injected into the bloodstream of a patient. Combination of Iodide and water or blood, which consists mainly of water, and a combination of calcium deposits and soft tissue exhibit similar material densities, resulting in poor spatial and low contrast resolution between each combination and having effectively similar corresponding brightness levels when viewed by a practitioner. It is undesirable to have calcium build-up on inner linings of blood vessel walls. Thus, the practitioner, due to difficulty in discerning between the brightness levels of reconstructed CT images for the stated combinations, may not be able to determine whether there exists a calcium build-up in the blood vessels of the patient.

Referring now to FIG. 1, a cross-sectional view of a traditional CT tube assembly 10 is shown. CT imaging systems include a gantry that rotates at various speeds in order to create a 360 Å° image. The gantry contains the CT tube assembly 10, which generates x-rays across a vacuum gap 12 between a single cathode 14 and an anode 16. In order to generate the x-rays, a large voltage potential is created across the vacuum gap 12 allowing electrons, in the form of an electron beam, to be emitted from the cathode 14 to a single target 18 of the anode 16. In releasing of the electrons, a filament contained within the cathode 14 is heated to incandescence by passing an electric current therein. The electrons are accelerated by the high voltage potential and impinge on the target 18, whereby they are abruptly slowed down to emit x-rays and form an x-ray beam that passes through a CT tube window 20.

After passing through the CT tube window 20 the x-ray beam is filtered, via a single filter 22. The filter 22 reduces number of low energy x-rays that have energy levels below a predetermined energy level, thus reducing x-ray exposure to a patient. An example of a pre-patient energy spectrum plot of number of x-rays versus corresponding energy levels is shown in FIG. 2. A post-filter spectrum curve 24 overlays an approximate pre-filter spectrum curve 26. Notice that the spectrum curve 24 is single peaked and that the number of x-rays corresponding to energy levels below 40 KeV are significantly reduced, due to absorption by the filter 22.

The post filter x-rays pass through a portion of the patient and are detected by an x-ray detector array. As the x-rays pass through the patient, the x-rays become attenuated before impinging upon the detector array. X-ray attenuation measurements are generated by the x-ray detector corresponding to electrical signal response generated by the received x-rays having varying energy levels depending upon attenuation thereof. An x-ray image is reconstructed in response to the attenuation measurements.

The x-ray detector array generates an x-ray signal in response to the single peaked energy spectrum. Number of x-rays received by the detector is integrated over an average area of the detector and over a view time interval to generate an integrated signal. The integrated signal is directly related to densities of scanned materials of the patient. As is known in the art, it is difficult from the resulting energy spectrum and from inherent characteristics of integration to differentiate between similar material densities.

It would therefore be desirable to provide a CT system of energy discrimination to differentiate between different scanned materials and different scanned material combinations to increase CT scanning utility and capability. It would also be desirable for the CT system to be capable of performing energy discrimination with accuracy, clarity, and without increased x-ray exposure to a patient.

SUMMARY OF INVENTION

The present invention provides system and method of performing energy discrimination within an imaging system. An x-ray source for performing energy discrimination within an imaging system is provided and includes a cathode-emitting device emitting electrons and an anode that has a target whereupon the electrons impinge to generate an x-ray beam with multiple x-ray quantity energy peaks.

A method of performing energy discrimination in the imaging system is also provided, which includes emitting the electrons. The x-ray beam with the x-ray quantity energy peaks is generated. The x-ray beam is directed through an object and is received. An x-ray image having multiple energy differentiable characteristics is generated in response to the x-ray beam.

One of several advantages of the present invention is that it provides a system that is capable of performing energy discrimination, thus allowing a practitioner to differentiate between materials and material combinations having similar densities. In so doing, the present invention provides an increased yield of information for improved diagnostic, examination, testing, and evaluation purposes.

Another advantage of the present invention is that it provides improved spatial and low contrast resolution between different materials, thus further providing increased ease in differentiating between scanned materials.

Furthermore, the present invention provides energy discrimination while minimizing x-ray exposure to a patient.

The present invention itself, together with attendant advantages, will be best understood by reference to the following detailed description, taken in conjunction with the accompanying figures.

BRIEF DESCRIPTION OF DRAWINGS

For a more complete understanding of this invention reference should now be had to the embodiments illustrated in greater detail in the accompanying figures and described below by way of examples of the invention wherein.

DETAILED DESCRIPTION

Figure 1:
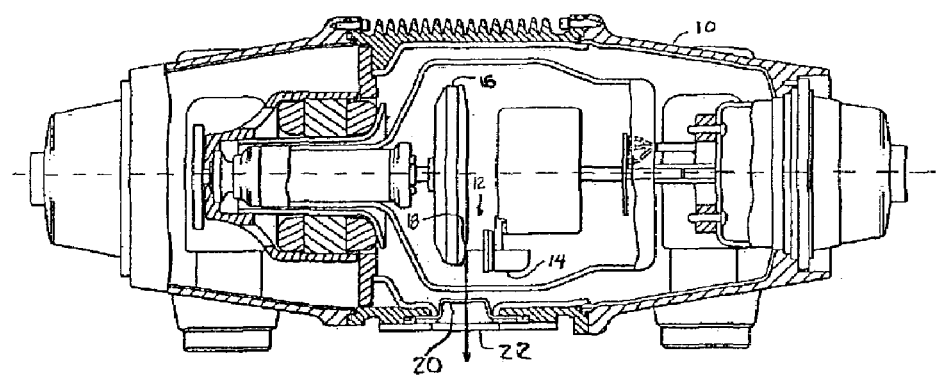
FIG. 1 is a cross-sectional view of a traditional CT tube assembly.
Figure 2:
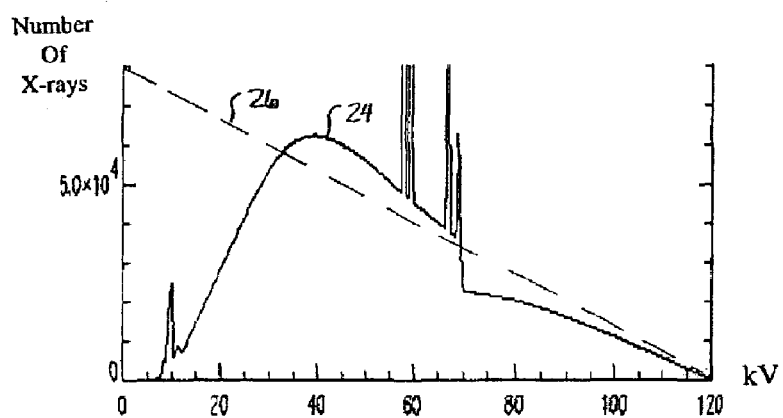
FIG. 2 is a pre-patient energy spectrum plot for the CT tube assembly of FIG. 1.

In each of the following figures, the same reference numerals are used to refer to the same components. While the present invention is described with respect to system and method of performing energy discrimination within a computed tomography (CT) imaging system, the following apparatus and method is capable of being adapted for various purposes and is not limited to the following applications: MRI systems, CT systems, radiotherapy systems, X-ray imaging systems, ultrasound systems, nuclear imaging systems, magnetic resonance spectroscopy systems, and other applications known in the art.

In the following description, various operating parameters and components are described for one constructed embodiment. These specific parameters and components are included as examples and are not meant to be limiting.

Also, in the following description the term "x-ray quantity energy peaks" refers to general shape of an energy spectrum plot and peaks contained therein. An energy spectrum plot being a plot of x-ray energy levels and corresponding number of x-rays for each energy level. X-ray quantity energy peaks does not refer to sporadic spikes or minor or other insignificant data that may occur or exist within the energy plot. See FIG. 8 description below for a further detailed explanation.

Figure 3:
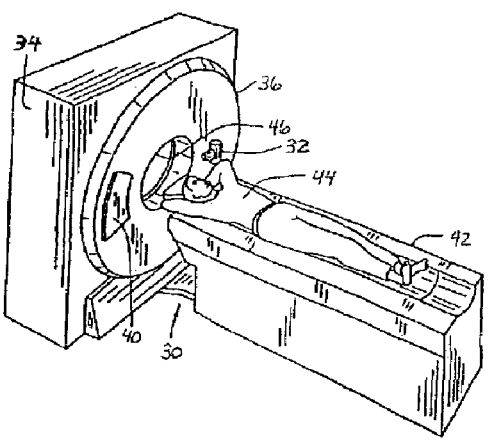
FIG. 3 is a perspective view of a CT imaging system including an x-ray source in accordance with an embodiment of the present invention.

Referring now to FIG. 3, a perspective view of a CT imaging system 30 including an x-ray source 32 in accordance with an embodiment of the present invention is shown. The imaging system 30 includes a gantry 34 that has a rotating inner portion 36 containing the x-ray source 32 and an energy-differentiating detector 40. The x-ray source 32 projects a beam of x-rays having multiple x-ray quantity energy peaks towards the detector 40. The source 32 and the detector 40 rotate about an operably translatable table 42. The table 42 is translated along a z-axis between the source 32 and the detector 40 to perform a helical scan. The beam after passing through a medical patient 44, within a patient bore 46, is detected at the detector 40 to generate projection data that is used to create a CT image.

Figure 4:
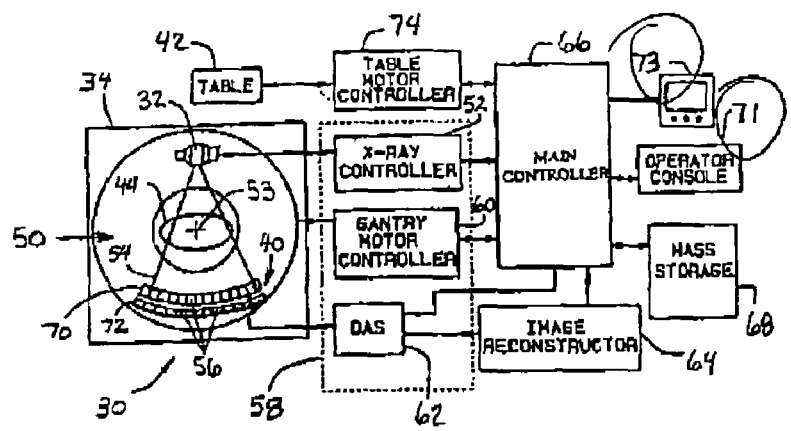
FIG. 4 is a cross-sectional close-up block diagrammatic view of a CT imaging system utilizing an energy discrimination system in accordance with an embodiment of the present invention.

Referring now to FIG. 4, a cross-sectional close-up block diagrammatic view of the imaging system 30 utilizing an energy discrimination system 50 in accordance with an embodiment of the present invention is shown. The energy discrimination system 50 includes the source 32, the detector 40, and an x-ray controller 52.

Generally, in operation the source 32 and the detector 40 rotate about a center axis 53. The beam 54 is received by multiple detector elements 56. Each detector element 56 generates an electrical signal corresponding to intensity of the impinging x-ray beam 54. As the beam 54 passes through the patient 44 the beam 54 is attenuated. Rotation of the inner portion 36 and operation of source 32 are governed by a control mechanism 58. Control mechanism 58 includes the x-ray controller 52 that provides power and timing signals to source 32 and a gantry motor controller 60 that controls the rotational speed and position of the inner portion 36. A data acquisition system (DAS) 62 samples analog data from the detector elements 56 and converts the analog data to digital signals for subsequent processing. An image reconstructor 64 receives sampled and digitized x-ray data from the DAS 62 and performs high-speed image reconstruction. A main controller 66 stores the CT image in a mass storage device 68.

The x-ray source 32 and the detector 40 rotate around an object to be imaged, such as the patient 44, so that the angle at which the beam intersects the object constantly changes. A group of x-ray attenuation measurements, i.e., projection data, from the detector 40 at one gantry angle is referred to as a "view." A "scan" of the object comprises a set of views made at different gantry angles during one revolution of the x-ray source 32 and the detector 40. In an axial scan, the projection data is processed so as to construct an image that corresponds to two-dimensional slices taken through the object.

One method for reconstructing an image from a set of projection data, projection data referring to a group of attenuation measurements, is referred to as the "filtered back-projection technique." This process converts the attenuation measurements from a scan into discrete integers, ranging from 1024 to +3072, called "CT numbers" or "Hounsfield Units"(HU). These HU's are used to control the brightness of a corresponding pixel on a cathode ray tube or a computer screen display in a manner responsive to the attenuation measurements. For example, an attenuation measurement for air may convert into an integer value of 1000 HU"s (corresponding to a dark pixel) and an attenuation measurement for very dense bone matter may convert into an integer value of +3000 (corresponding to a bright pixel), whereas an attenuation measurement for water may convert into an integer value of 0 HU's (corresponding to a gray pixel). This integer conversion, or "scoring" allows a physician or a technician to determine the density of matter based on the intensity of the computer display and thus locate and identify areas of concern.

In one embodiment of the present invention, the detector 40 includes a first detector array 70 and a second detector array 72, as shown. The first array 70 may be a scintillator detector/photo-sensor detector so as to allow for the collection of traditional information for creating anatomical detail for CT slices. The second array 72 may be a direct conversion (DC) detector, such as a cadmium zinc telluride detector, configured in an x-ray counting and energy discrimination mode to count attenuated x-rays and to measure attenuated x-ray energy.

Number and energy of the attenuated x-rays is used when performing energy discrimination to differentiate between material characteristics. Elemental composition and/or density of various tissue materials may be determined, such as differentiating between iodine, blood, calcium, or other materials known in the art. Information obtained from the arrays 70 and 72 may be super positioned to create a single image having identically positioned and overlapping information of anatomical detail and/or tissue discrimination (material type and density).

The second array 72 may be of a single slice design and/or a multiple slice design. The multiple slice design may provide information on a variety of different tissue materials, whereas the multiple slice design may be integrated across multiple slices for improved statistics on an individual basis. When the second array 72 is used in the x-ray counting and energy discrimination mode, x-ray dose added to the CT exam is minimized since a low quantity of x-rays are used to perform energy discrimination. To gather energy discrimination data a smaller amount of x-rays are used over a full or normal dose of x-rays, as used in a normal CT scan. A normal CT scan is performed with the first array 70 to provide detailed data, such as detailed anatomical data. When gathering energy discrimination data the second array 72 is used to generate an overlay image with material differentiating characteristics, such as tissue differentiating characteristic.

The above-described embodiment is for example purposes only. Although, it is preferred that at least one array be capable of detecting numbers of x-rays for various energy levels or ranges of energy levels, which are hereinafter referred to as x-ray quantity energy levels, any number of arrays may be used. For example, in the above-described embodiment array 72 is capable and configured to detect x-ray quantity energy levels, whereas array 70 is not. Also, each of the arrays 70 and 72 may be of various type and style and be in various configurations known in the art.

For a further detailed description of the detector 40 and possible embodiments thereof see application Ser. No. 10/064,775, now U.S. Pat. No. 6,819,738, entitled "A Hybrid Scintillator/Photo Sensor and Direct Conversion Detector", incorporated by reference herein.

The main controller 66 also receives commands and scanning parameters from an operator via an operator console 71. A display 73 allows the operator to observe the reconstructed image and other data from the main controller 66. The operator supplied commands and parameters are used by the main controller 66 in operation of the x-ray controller 52, the gantry motor controller 60, and the DAS 62. In addition, the main controller 66 operates a table motor controller 74, which translates the table 42 to position patient 44 in gantry 34.

The x-ray controller 52, the gantry motor controller 60, the image reconstructor 64, the main controller 66, and the table motor controller 74 are preferably based on micro processors, such as a computer having a central processing unit, memory (RAM and/or ROM), and associated input and output buses. The x-ray controller 52, the gantry motor controller 60, the image reconstructor 64, the main controller 66, and the table motor controller 74 may be a portion of a central control unit or may each be stand-alone components as shown.

In the following embodiments a cathode-emitting device may refer to any electron emitting device or component. A cathode-emitting device may refer to a cathode, an x-ray tube kVp, a cathode-emitting surface, a cathode element, or other electron emitting device or component known in the art.

Figure 5:
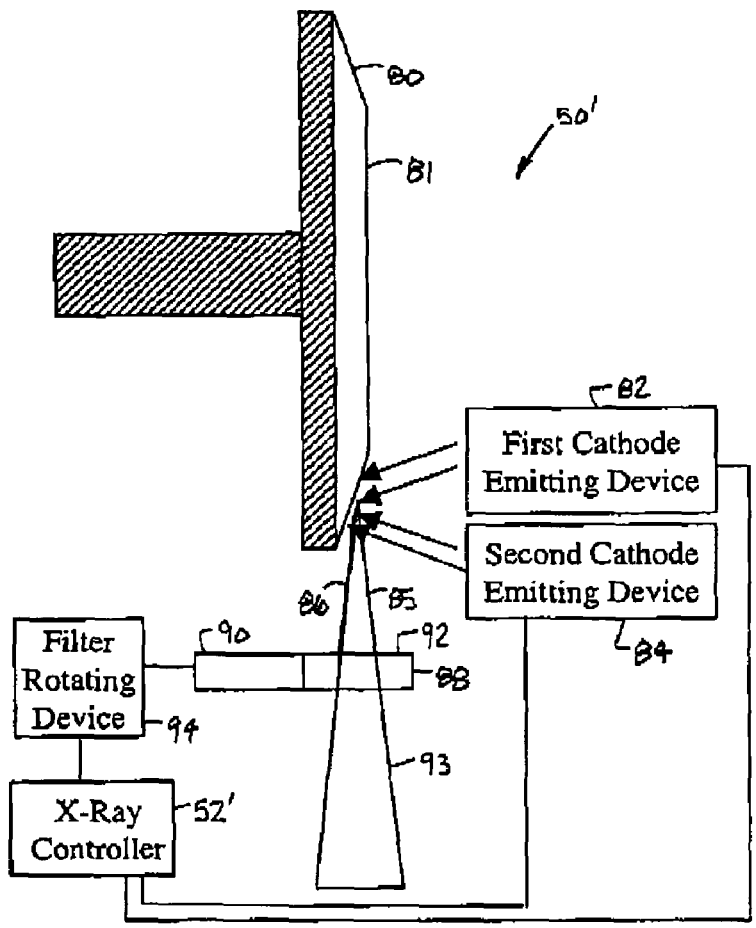
FIG. 5 is a cross-sectional close-up block diagrammatic view of an energy discrimination system having a single anode target in accordance with an embodiment of the present invention.

Referring now to FIG. 5, a cross-sectional close-up block diagrammatic view of an energy discrimination system 50' having a single rotating target 80 of an anode 81 in accordance with an embodiment of the present invention is shown. A first cathode-emitting device 82 and a second cathode-emitting device 84 emit electrons that are directed to impede upon the target 80. A first kVp exists between the first cathode-emitting device 82 and the anode target 80, which can be represented by a first approximately linear pre-filter spectrum curve of number of x-rays per energy level. A second kVp, that is different from that of the first kVp, exists between the second cathode-emitting device and the anode target 80, which can be represented by a second approximately linear pre-filter spectrum curve of number of x-rays per energy level. The pre-filter spectrum curves may be represented using Cramer's Rule, as known in the art. The first kVp pre-filter spectrum curve is different in slope than that of the second kVp pre-filter spectrum curve.

Upon impact with the target 80, x-rays in the form of x-ray beams 85 and 86 are generated and directed through a rotating filter 88. The rotating filter 88 includes a first filter 90 and a second filter 92; each of the filters 90 and 92 have different energy absorbing characteristics. Although, a rotating filter is utilized, some other filtering device having two or more filters may be used. In one embodiment, each filter 90 and 92 prevent passage of x-rays corresponding to energy levels below associated predetermined energy levels for each of the x-ray beams 85 and 86. In effect the filters 90 and 92, for the stated embodiment, are acting as low pass filters. Of course, the filters may perform as band pass, notch, high pass, digital, or other type of filter known in the art.

The x-ray beams 85 and 86 are mixed upon passing through the filters 90 and 92 to generate a post-filter beam 93 having multiple x-ray quantity energy peaks, due to generation of different quantities of electrons at associated energy levels therein by the devices 82 and 84 and different absorbing characteristics of the filters 90 and 92. The filters 90 and 92 in effect may have different energy pass ranges, so as to allow x-rays within a predetermined energy range to pass through the filters 90 and 92. The energy pass ranges may be of any size and be associated with any energy level or levels.

An x-ray controller 52', is electrically coupled to the devices 82 and 84 and to a filter rotating device 94, which is coupled to and rotates the filter 88. The controller 52', synchronously transitions between the devices 82 and 84 and the filters 90 and 92, respectively. The controller 52' may be in the form of or an integral part of the x-ray controller 52 or the main controller 66, may be a separate controller, or may be some other controller known in the art.

Figure 6:
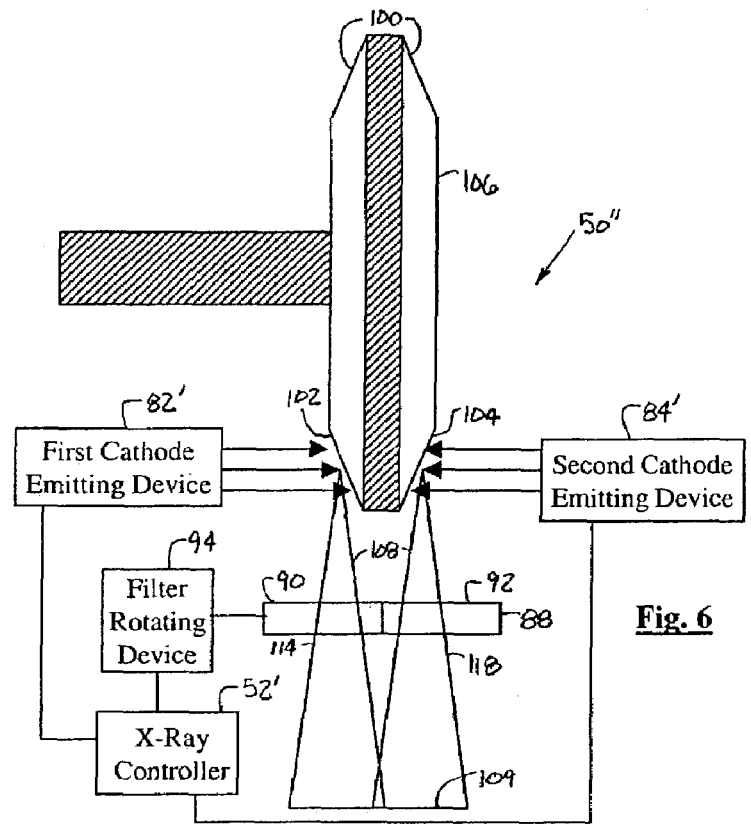
FIG. 6 is a cross-sectional close-up block diagrammatic view of an energy discrimination system having dual anode targets in accordance with another embodiment of the present invention.
Figure 8:
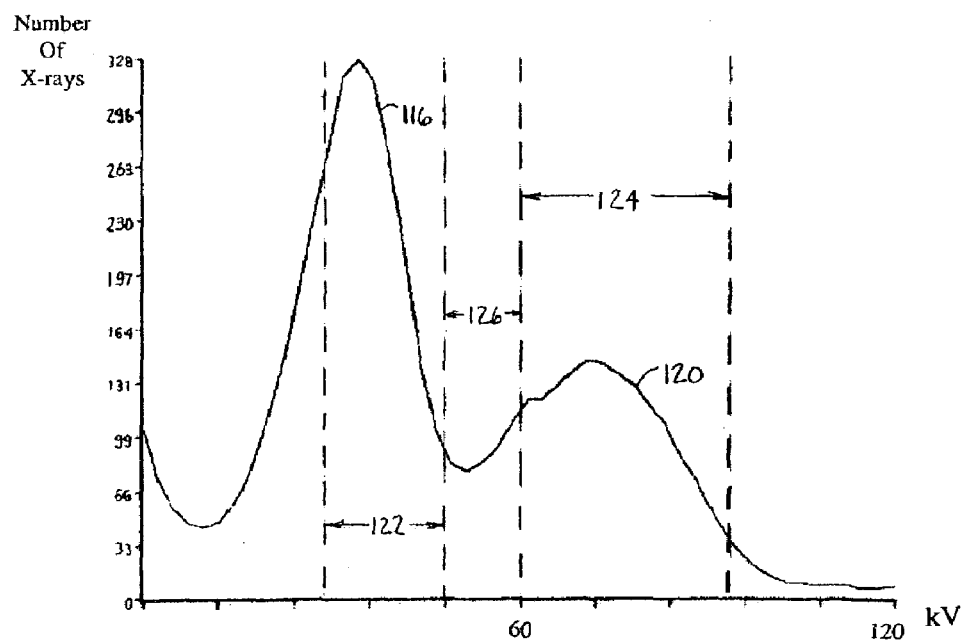
FIG. 8 is a pre-patient energy spectrum plot for an x-ray source in accordance with another embodiment of the present invention.

Referring now to FIG. 6, a cross-sectional close-up block diagrammatic view of an energy discrimination system 50" having dual anode rotating targets 100 in accordance with another embodiment of the present invention is shown. A first cathode-emitting device 82' and a second cathode-emitting device 84' emit electrons that are directed to impede upon a first rotating target 102 and a second rotating target 104 of an anode 106, respectively. A first kVp exists between the first cathode-emitting device 82' and the rotating target 102 and a second kVp exists between the second cathode-emitting device 84' and the rotating target 104, in a similar fashion as to that of the embodiment of FIG. 5. Upon impact with the targets 102 and 104, x-rays in the form of x-ray beams 108 are generated and directed through the rotating filter 88, whereupon exiting the filter 88 they are mixed to generate a post filter beam 109. Although the rotating filter 88 is utilized, some other filtering device having one or more filters may be used. The filters 90 and 92 may be transitional or may be stationary. The beam 109 has two or more x-ray quantity energy peaks, as is best seen in FIG. 8.

As with the embodiment of FIG. 5, the controller 52' is electrically coupled to the emitting devices 82' and 84' and to the filter rotating device 94, which is coupled to and rotates the filter 88. The controller 52', synchronously transitions between the devices 82' and 84' and the filters 90 and 92, respectively. In an alternative embodiment, the filters 90 and 92 are stationary and the devices 82' and 84' are operated simultaneously.

FIGS. 5 and 6 illustrate two possible embodiments of the present invention, other embodiments may be easily envisioned by one skilled in the art. There may exist any number of anode targets, cathode-emitting devices, and filters. For example, the first cathode-emitting device 82 and the second cathode-emitting device 84 may be replaced by a single cathode-emitting device operating so as to generate and transition between two different kVps. Also, more than two cathode-emitting devices and/or filters may be used to generate a beam having any number of x-ray quantity energy peaks. These examples are described in further detail below.

Although, it is preferred for accuracy, resolution, and clarity purposes to have at least two cathode-emitting devices and at least two filters, as is shown in the embodiments of FIGS. 5 and 6, various quantities of each may be used.

In a couple alternative embodiments of the present invention, the embodiments of FIGS. 5 and 6 are modified such that only a single cathode-emitting device is used in combination with the rotating filter 88. The first filter 90 and the second filter 92 are alternated therebetween for a single x-ray beam to generate a post-patient x-ray beam having a dual peaked energy spectrum. The single cathode-emitting device may have a quickly varying kVp, which may be used in conjunction with a transitioning or rotating filter.

In a further pair of alternative embodiments of the present invention, the embodiments of FIGS. 5 and 6 are modified, such that the cathode-emitting devices 82, 82', 84, and 84' are utilized in conjunction with a single stationary filter instead of the rotating filter 88. The cathode-emitting devices 82 and 84 and the cathode-emitting devices 82' and 84' are alternated, respectively, therebetween to generate x-ray beams having different energy spectrum profiles or distributions of the number of x-rays per energy level.

Figure 7:
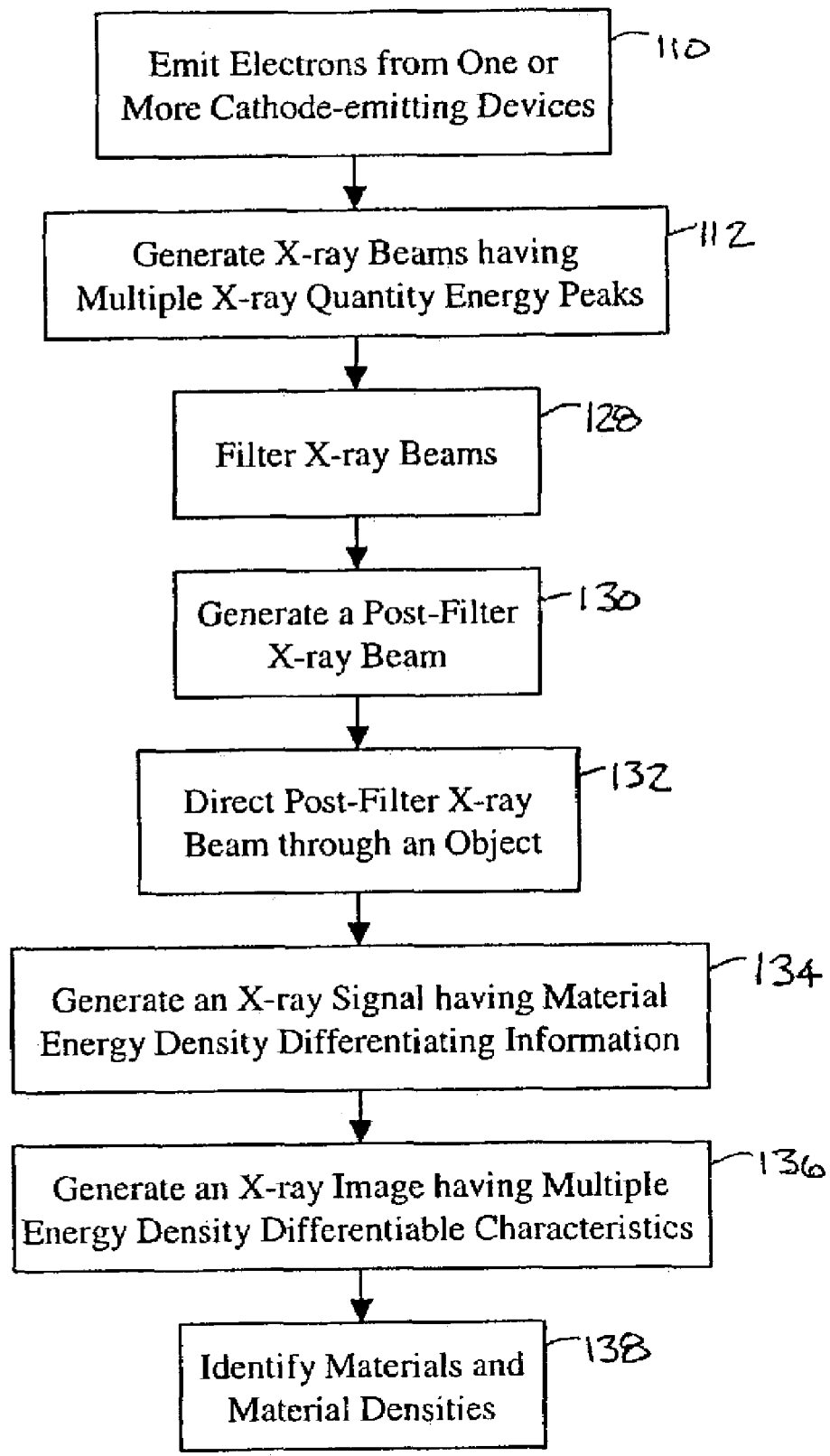
FIG. 7 is a logic flow diagram illustrating a method of performing energy discrimination in an imaging system in accordance with an embodiment of the present invention.

Referring now to FIG. 7, a logic flow diagram illustrating a method of performing energy discrimination in an imaging system in accordance with an embodiment of the present invention is shown. For simplicity, the method of FIG. 7 is described with respect to the embodiments of FIGS. 5 and 6, but is not limited to the stated embodiments.

In step 110, one or more cathode-emitting devices emit electrons, such as emitting devices 82, 82', 84, and 84', to impinge upon one or more anode targets, such as targets 80, 102' and 104, as described above.

In step 112, x-ray beams, such as beams 86 and 108, are generated having multiple x-ray quantity energy peaks. For example, a first x-ray beam 114 having a first x-ray quantity energy peak 116 and a second x-ray beam 118 having a second x-ray quantity energy peak 120 may be generated; beams 114 and 118 are best seen in FIG. 6 and peaks 116 and 120 are best seen in the pre-patient energy spectrum plot of FIG. 8. The first x-ray quantity energy peak 116 and the second x-ray quantity energy peak 120 are generated by respective kVp of each cathode-emitting device 82' and 84' and filtering of each x-ray beam 108 by the filters 90 and 92.

Although, in this described embodiment the energy spectrum plot has only a pair of peaks 116 and 120, an energy spectrum plot may have any number of peaks, by altering the number of cathode-emitting devices, filters, and correlations between the cathode-emitting devices and the filters. The peaks 116 and 120 may correspond to predetermined energy bins 122 and 124, as shown, which may be separated by one or more separation zones 126 (only one is shown) having significantly reduced quantities of x-rays. The bins 122 and 124 and the separation zones 126 aid in accurately differentiating between materials having similar material energy densities.

Referring again to FIG. 7, in step 128, the x-ray beams are filtered, via the rotating filter 88. The controller 52' transitions between the first filter 90 and the second filter 92. The controller 52' transitions between the filters 90 and 92 at least once for each view in a scan of the patient 44.

In step 130, the x-ray beams are mixed to generate a post-filter x-ray beam, such as beams 93 and 109, having multiple x-ray quantity energy peaks.

In step 132, the post-filter x-ray beam is directed through at least a portion of the patient 44.

In step 134, the detector 40 receives the post-filter x-ray beam and in response thereto generates an x-ray signal having material energy density differentiating information, such as numbers of x-rays per energy level, contained therein. The x-ray detector 40 may measure x-ray quantity energy levels of the x-ray beams corresponding to each of the peaks 116 and 120 and may measure x-ray quantity energy levels corresponding to the energy bins 122 and 124 to aid in simplifying energy discrimination of multiple materials having similar energy densities. The detector 40 or other signal conditioning devices known in the art may signal condition the x-ray signal such that separations between x-ray quantity energy peaks are effectively magnified, by filtering out energy densities below and above undesired predetermined energy density levels.

In step 136, the system 30 generates an x-ray image having multiple energy density differentiable characteristics, such as image contrast levels, brightness levels, color variations, or other differentiating characteristic known in the art, in response to the x-ray signals.

In step 138, materials and material densities of the scanned portion of the patient 44 are identified. The materials and material densities may be determined by a practitioner, by the main controller 66, or by some other device or technique known in the art. In having multiple x-ray energy peaks, materials or material combinations having similar densities may be easily differentiated, since each material or material combination exhibits different x-ray energy peak profiles.

The x-ray energy peak profiles may be further used to generate different image material differentiating characteristics. For example, a first material combination may exhibit a dual peaked energy spectrum having a first magnitude set of values for each peak and a second material combination may also exhibit a dual peaked energy spectrum, but having a second and different magnitude set of values for each peak. The differences in magnitude or peak values between the two material combinations may be illustrated in an x-ray image through use of one or more of the above-mentioned differentiating characteristics.

The above-described steps are meant to be an illustrative example; the steps may be performed synchronously, sequentially, simultaneously, or in a different order depending upon the application.

The present invention provides an energy discrimination system and method for easily differentiating between materials and material combinations that have similar energy densities. The present invention provides this increased performance capability and improved spatial and low contrast resolution while minimizing x-ray exposure to a patient.

The above-described apparatus, to one skilled in the art, is capable of being adapted for various purposes and is not limited to control systems or other communication systems. The above-described invention may also be varied without deviating from the spirit and scope of the invention as contemplated by the following claims.

The invention claimed is:

1. An x-ray source for performing energy discrimination within an imaging system comprising:
   a plurality of cathode-emitting devices emitting a plurality of electrons; and
   a single rotating anode having a plurality of targets oriented whereupon said plurality of electrons impinge to generate a plurality of x-ray beams; and
   a plurality of filters simultaneously filtering said plurality of x-ray beams to generate a post-filter x-ray beam having an x-ray distribution with simultaneously a plurality of x-ray quantity versus energy peaks defined as a plurality of peaks in the number of x-rays at multiple energy levels.

2. An x-ray source as in claim 1 wherein said a plurality of cathode-emitting device comprises:
   a first cathode-emitting device emitting a first plurality of electrons; and
   a second cathode-emitting device emitting a second plurality of electrons.

3. An x-ray source as in claim 2 wherein said first cathode-emitting device emits said first plurality of electrons at a first kVp and said second cathode-emitting device emits said second plurality of electrons at a second kVp.

4. An x-ray source as in claim 1 wherein said plurality of filters comprises a stationary filter.

5. An x-ray source as in claim 1 wherein said plurality of filters comprises a rotating filter.

6. An x-ray source as in claim 1 wherein said plurality of filters comprises:
   a first filter filtering a first x-ray beam; and
   a second filter filtering a second x-ray bear.

7. An x-ray source as in claim 1 comprising:
   a first filter having a first energy pass range; and
   a second filter having a second energy pass range.

8. An x-ray source as in claim 1 wherein said plurality of targets are on different sides of said single rotating anode.

9. An x-ray source as in claim 1 wherein said plurality of targets are on different surfaces of said single rotating anode.

10. An imaging system comprising:
    an x-ray source comprising;
    a plurality of cathode-emitting devices emitting a plurality of electrons; and
    at least one anode having at least one target oriented relative to said plurality of cathode-emitting devices whereupon said plurality of electrons impinge to generate a plurality of x-ray beams; and
    a plurality of filters simultaneously filtering said plurality of x-ray beams to generate a post-filter x-ray beam having simultaneously a plurality of x-ray quantity versus energy peaks defined as a plurality of peaks in the quantity of x-rays at a plurality energy levels; and
    an energy differentiating detector receiving said post-filter x-ray beam and generating an x-ray signal having material energy density differentiating information.

11. An imaging system as in claim 10 comprising:
    a filter rotating device coupled to said plurality of filters; and
    a controller electrically coupled to said filter rotating device and rotating said plurality of filters.

12. An imaging system as in claim 11 wherein said controller transitions between each filter in said plurality of filters for each view within a plurality of views.

13. An imaging system as in claim 10 further comprising an x-ray detector measuring a plurality of x-ray quantity energy levels of said x-ray beam.

14. An imaging system as in claim 13 wherein said x-ray detector measures said plurality of x-ray quantity energy levels corresponding to each of said plurality of x-ray quantity peaks.

15. An imaging system as in claim 13 wherein said x-ray detector measures said plurality of x-ray quantity energy levels in at least one energy bin.

* * * * *